United States Patent [19]

Borden et al.

[11] Patent Number: 4,891,449

[45] Date of Patent: Jan. 2, 1990

[54] HALOGENATED UNSYMMETRICAL HIGHER ALKYL PHENOXY ALKANES

[75] Inventors: Dennis M. Borden, West Lafayette; Nicolai A. Favstritsky; Enrico J. Termine, both of Lafayette, all of Ind.

[73] Assignee: Great Lakes Chemical Corporation, West Lafayette, Ind.

[21] Appl. No.: 213,540

[22] Filed: Jun. 30, 1988

[51] Int. Cl.$^4$ .......................................... C07C 43/225
[52] U.S. Cl. .................................. 568/645; 568/592
[58] Field of Search ............................ 568/592, 645

[56] References Cited

U.S. PATENT DOCUMENTS

| | | |
|---|---|---|
| 3,660,351 | 5/1972 | Schmidt et al. ............... 524/288 |
| 3,810,866 | 5/1974 | Anderson ..................... 260/45.9 R |
| 3,833,538 | 9/1974 | Anderson ..................... 260/45.9 R |
| 3,833,539 | 9/1974 | Anderson ..................... 260/45.9 R |
| 3,862,085 | 1/1975 | Anderson ..................... 260/45.9 R |
| 3,869,425 | 3/1975 | Anderson ..................... 260/45.9 R |
| 3,876,611 | 4/1975 | Anderson ..................... 260/45.9 R |
| 3,883,479 | 5/1975 | Anderson et al. ............... 524/208 |
| 4,016,137 | 4/1977 | Anderson ..................... 260/45.75 R |
| 4,059,561 | 11/1977 | Arai et al. ..................... 524/319 |
| 4,171,330 | 10/1979 | Kyo et al. ...................... 524/172 |
| 4,567,218 | 1/1986 | Petiet .......................... 524/373 |

Primary Examiner—Donald B. Moyer
Assistant Examiner—Karen E. Plue
Attorney, Agent, or Firm—Kirkland & Ellis

[57] ABSTRACT

Halogenated unsymmetrical higher alkyl bisphenoxy alkanes having utility as non-blooming flame retardant agents.

8 Claims, No Drawings

HALOGENATED UNSYMMETRICAL HIGHER ALKYL PHENOXY ALKANES

BACKGROUND OF THE INVENTION

1. Field of Invention

The present invention relates to a plastic additive composition and more particularly to a plastic additive composition comprising halogenated unsymmetrical higher alkyl bisphenoxy alkanes.

2. Description of the Art

Traditionally, plastic additive compositions are an important class of industrial materials. Plastic additives are used to enhance or modify the properties of commercially available polymers. The use of plastic additives allows a relatively small number of commercially available polymers to be tailored to a myriad of uses. Those skilled in the art will know that the selection of an application specific plastic additive is unpredictable at best. Therefore, additive manufacturers must take a sophisticated approach and offer a range of products to achieve the desired result.

Plastic additive compositions can be used as plasticizers, flame retardants, flow modifiers, or impact modifiers in resin systems, heat transfer fluids, or hydraulic fluids.

One important use of plastic additive compositions is as flame retardants in resin systems. Most flame retardants, although efficient in their function of retarding the rate of combustion in a resin system, have a tendency to affect adversely one or more key properties of he resin. For example, many flame retardant additives tend to reduce the impact strength of the resin; to migrate from the resin composition, resulting in a phenomena known as "bloom"; to volatilize from the resin composition; to plasticize the resin composition adversely, and therefore lowering the heat deflection temperature, etc.

A number of flame retardants are used specifically in acrylonitrile-butadiene-styrene ("ABS") resins, for example. The following compositions have all been used in ABS systems: bis(tribromophenoxy)-ethane, octabromodiphenyl ether, decabromodiphenyl ether, tetrabromobisphenol-A and its carbonate oligomers, and bis(pentabromophenoxy)-ethane. Among the prior art specifically dealing with flame retarding ABS resins are U.S. Pat. No. 4,016,134 and U.S. Pat. No. 4,567,218 and references cited therein. These flame retardant agents for ABS plastics have not been entirely satisfactory because of problems of "bloom", light instability, discolortion, and adverse effects on properties such as impact strength and flowability.

Anderson, et al., in a series of patents disclose plastic compositions containing flame retardants. The flame retardants are bisphenoxy compounds having the general formula

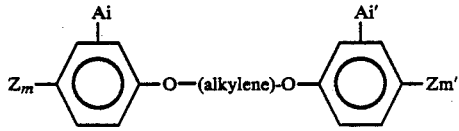

wherein Z is bromine, m and m' are integers having a value of 1-4, i and i' are integers having a value of 1 or 2, alkylene is a straight or branched claim alkylene group having 1 to 6 carbon atoms, and A is cyano, nitro, lower alkoxy, lower alkyl (defined as $CH_3$, $C_2H_5$, $C_3H_7$, or $C_4H_9$), flourine, dialkylamino, phenyl, halo-phenyl, benzyl or halo-benzyl. (See U.S. Pat. Nos. 3,810,866; 3,833,538; 3,883,479; 3,883,539; 3,862,085; 3,869,425; and 3,876,711). The plastic compositions containing the symmetrical bisphenoxy compounds include a plastic material in the composition such as polystyrene, ABS, polyester, poly(phenylene oxide), polyurethane and other polyolefins. These patents fail to suggest a plastic additive composition comprising halogenated unsymmetrical or higher alkyl substituted bisphenoxy compounds.

Accordingly, a primary object of this invention is to provide new unsymmetrical higher alkyl halogenated bisphenoxy alkanes.

Another object of the invention is to provide halogenated unsymmetrical higher alkyl bisphenoxy alkanes having utility as flame retardant agents.

Yet another object of the invention is to provide halogenated unsymmetrical higher alkyl bisphenoxy alkanes having utility as non-blooming flame retardants.

SUMMARY OF THE INVENTION

The foregoing and other objects, advantages and features of this invention may be achieved with new compositions of matter comprising halogenated unsymmetrical higher alkyl bisphenoxy alkanes. Preferably the bisphenoxy alkanes used in accordance with this invention is a brominated unsymmetrical higher alkyl bisphenoxy ethane. The preferred brominated bisphenoxy ethane contains between 40 and 70 percent by weight of bromine.

DETAILED DESCRIPTION OF THE PREFERRED EMBODIMENTS

In accordance with this invention, new halogenated unsymmetrical higher alkyl bisphenoxy compounds have been discovered. The novel compositions of this invention are distinguished from the known bisphenoxy compositions by improved properties. The novel compositions are stable to light and heat, have good flame retardant properties, and, most importantly, compositions incorporating the novel compounds do not bloom.

The novel compositions of matter are halogenated unsymmetrical higher alkyl bisphenoxy alkanes of the following formula:

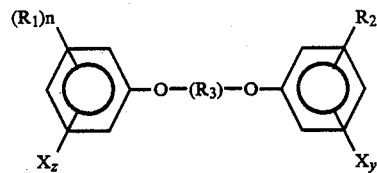

wherein X is bromine or chlorine; z is an integer from 2 to 5; $R_1$ is an alkyl ranging from methyl ($CH_3$) to dodecyl ($C_{12}H_{25}$); n is 0, 1, or 2; y is 0, 1, or 2; $R_2$ is an alkyl selected from the group consisting of sec-butyl, (sec $C_4H_9$), pentyl ($C_5H_{11}$) hexyl ($C_6H_{13}$) heptyl ($C_7H_{15}$), octyl ($C_8H_{17}$), nonyl ($C_9H_{19}$), decyl ($C_{10}H_{21}$), undecyl ($C_{11}H_{23}$) and dodecyl ($C_{12}H_{25}$). $R_3$ is a straight or branched alkylene group from methyl ($CH_3$) to dodecyl ($C_{12}H_{25}$) such as cyclohexane for example; and such that if n is 1, $R_1$ is not $R_2$. The novel composition of matter contains some minor amounts of symmetrical halogenated higher alkyl bisphenoxy alkanes. The minor amounts in the composition do not effect the utility of the composition as a non-blooming flame retardant agent.

When X is bromine, the bromine content should be between approximately 40 percent and 70 percent by weight. Especially preferred bisphenoxy compounds, for example, are those compounds wherein x is 3, z is 2, and n is zero. In these most preferred compounds X is bromine, $R_2$ is either octyl ($C_8H_{17}$) or nonyl ($C_9H_{19}$) and $R_3$ is ethylene.

The halogenated unsymmetrical higher alkyl phenoxy alkanes can be used individually or in conjunction with other additives. The use of unsymmetrical bisphenoxy compounds in an ABS resin system is described in the Termine, et al., copending U.S. patent application entitled "Flame Retardant ABS Resin Compositions" filed herewith. When the preferred brominated bisphenoxy ethane is used in a plastic formulation, it should be employed in amounts of 0.5 to 30 percent by weight of the plastic formulation. The most preferred weight percent of brominated bisphenoxy ethane in the plastic formulation is 5 percent to 20 percent.

The preferred novel plastic additive compositions, brominated bisphenoxy ethanes are prepared in a two-step synthesis from brominated phenols and dihalogenated ethanes. The synthesis follows standard Williamson ether synthesis techniques, shown below without substitution:

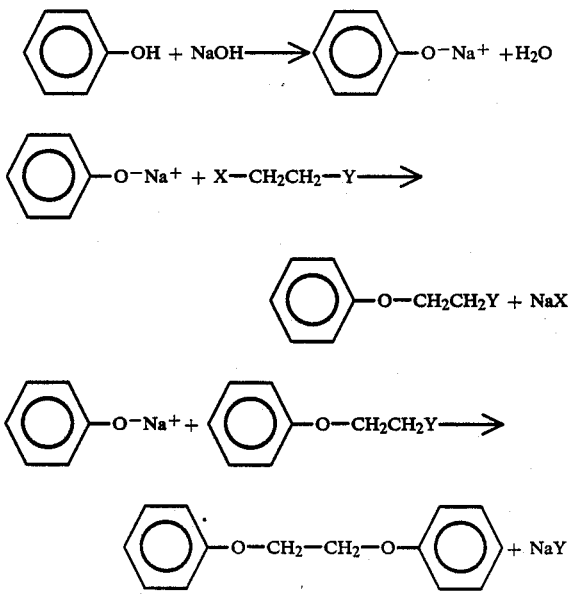

wherein X and Y are indepedently bromine or chlorine.

The preferred method of synthesis is to react the phenate salt containing the least alkyl content with a large excess of 1,2-dibromethane ($\geq 4$ moles/mole phenate) in a polar, high-boiling solvent such as propylene glycol. The excess dibromoethane is then preferably removed by distillation before reacting the intermediate with the second phenate salt.

The compounds listed in Table 1 are examples of compounds synthesized by the preferred synthesis method. The list is not intended to be exhaustive or to limit the scope of the invention. The brominated alkyl phenols were produced from commercially available alkyl phenols using techniques known in the art.

TABLE 1

| Compound | Z | Y | $R_1$ | n | $R_2$ | TGA, °C. 5% | 25% | 50% | % Br Theory | Found |
|---|---|---|---|---|---|---|---|---|---|---|
| A | 3 | 2 | — | 0 | $C_9H_{19}$ | 315 | 365 | 389 | 54.4 | 54.1 |
| B | " | 2 | — | " | $C_8H_{17}$ | 302 | 353 | 376 | 55.4 | 55.5 |
| C | " | 2 | — | " | $C_5H_{11}$ | 309 | 358 | 382 | 58.9 | 58.7 |
| D | " | 2 | — | " | $C_{12}H_{25}$ | 336 | 386 | 408 | 51.4 | 51.3 |
| E | " | 2 | $CH_3$ | 2 | $C_8C_{17}$ | 315 | 358 | 379 | 53.3 | 53.8 |
| G | 4 | 2 | $CH_3$ | 1 | $C_9H_{19}$ | 328 | 382 | 408 | 57.9 | 57.6 |
| H | 4 | 2 | $CH_3$ | 1 | $C_{12}H_{25}$ | 363 | 411 | 429 | 55.1 | 56.1 |
| I | 5 | 2 | — | 0 | $C_9H_{19}$ | 361 | 409 | 426 | 62.6 | 62.0 |
| M | 3 | 2 | — | 0 | Sec $C_4H_9$ | 313 | 363 | 387 | 60 | 59.5 |

EXAMPLES

The following preparations and examples are given to illustrate the invention and should not be construed as limiting its scope.

EXAMPLE 1

Step I:

2,4,6-Tribromophenol (856 grams, 2.6 moles), phenol (6 grams), sodium carbonate (180 grams, 1.7 moles) and propylene glycol (1036 grams) are combined in a five-liter reactor equipped with a mechanical stirrer. the mixture is brought to 100° C. with agitation and held for one hour. 1,2-Dibromoethane (1950 grams, 10.4 moles) is added to the reactor all at once. The temperature is returned to 100° C. and held for an additional three hours with high agitation. Without allowing the reaction mixture to cool, agitation is discontinued, the phases are allowed to separate. Methanol (6 liters) is placed in a 12-liter reactor with mechanical stirrer. With the methanol being vigorously agitated, the lower phase from the 5-liter reactor is added to the methanol while keeping the lower phase warm enough to avoid solidification before the addition is complete. The resulting methanol slurry is filtered to recover the product (β-bromoethyl-2,4,6-tribromophenyl ether, Compound Q). After drying in a vacuum oven at room temperature, 995 grams (87% of theory) of product with greater than 98% purity and less than one percent 1,2-bis(tribromophenoxy)-ethane are obtained.

Step II:

Dibromononylphenol (860 grams, 2.25 moles), phenol (5 grams), sodium carbonate (127 grams, 1.2 moles) and propylene glycol (2100 grams) are combined in a 5-liter reactor with mechanical stirrer. The mixture is heated slowly to 150° C. with agitation. Compound Q (995 grams, 2.25 moles) is added to the reaction portionwise over one hour at 150° C. with vigorous agitation. The temperature and agitation are maintained for an additional four hours. With the agitation off, the reaction is allowed to cool. The upper phase is decanted and the lower phase is dissolved in methylene chloride (1 liter). After washing with dilute hydrochloric acid, the solvent is distilled, and volatile components are removed using a wiped film evapoator at 200° C. and 1.0 torr vacuum. The product, Compound A, weighs 1530 grams (92.5%) of theory). Combined yield for the two steps is about 80% of theory.

EXAMPLE 2

Step I:
Dibromononylphenol (2270 grams, 6.0 moles), phenol (16 grams), sodium carbonate (382 grams, 3.6 moles) and propylene glycol (3700 grams) are combined in a 12-liter reactor equipped with a mechanical stirrer and a Dean-Stark trap. The mixture is slowly heated to 100° C. (30–60 minutes) with agitation and held at 100° C. for one hour. 1,2-Dibromoethane (4410 grams, 24.0 moles) is added to the reactor all at once. With vigorous agitation the mixture is heated to 130° C. and held for four hours. After cooling the reaction to 90°–95° C., water (300 grams) is added and the mixture heated to reflux (~95° C.). The dibromoethane and water azeotrope is collected in the Dean-Stark trap. The dibromoethane is removed and the water returned to the reactor until no additional dibromoethane is recovered. The water is then also removed. If during the azeotropic distillation the pH of the water becomes acidic, the situation is corrected by adding additional sodium carbonate to the reaction mixture.

Step II:
2,4,6-Tribromophenol (1985 grams, 6.0 moles), phenol (14 grams), sodium carbonate (382 grams, 3.6 moles) and propylene glycol (2500 grams) are combined in a 5-liter reactor equipped with a mechanical stirrer. The mixture is heated slowly to 100° C. (30–60 minutes) and held for one hour with agitation. The reaction mixture from Step I is heated to 145° C., and the contents of the 5-liter reactor are added to it. After returning the temperature to 145° C., the mixture is held at 145° C. with vigorous agitation for four hours. With the stirrer off, the reactor is cooled to 35° C. and the upper phase decanted. The lower phase is dissolved in methylene chloride (2.5 liter). After washing with dilute hydrochloric acid, the solvent is distilled, and volatile components are removed using a wiped film evaportor at 200° C. and 1.0 torr vacuum. The product, Compound A, weighs 3,480 grams, which is approximately 79% of its theoretical yield.

EXAMPLE 3

Step I:
Dibromononylphenol (983 grams, 2.6 moles), sodium carbonate (180 grams, 1.7 moles), 1,2-dibromoethane (1950 grams, 10.4 moles), tris(2-(2-methoxyethoxy)ethyl) amine or TDA-1 (84 grams) are combined in a 3-liter reactor equipped with a mechanical stirrer and Dean-Stark trap. The mixture is heated to 130° C. and held for four hours. After cooling, the mixture is filtered, and the excess dibromoethane is removed using a wiped film evaporator at 100° C. and 20 torr vacuum.

Step II:
The product from Step I which is predominantly β-bromoethyldibromononylphenyl ether and TDA-1 is combined with 2,4,6-tribromophenol (860 grams. 2.6 moles) and sodium carbonate (180 grams, 1.7 moles) in a 3-liter reactor equipped with mechanical stirrer and Dean-Stark trap. The mixture is heated to 130° C. and held for five hours. Methylene chloride (2 liters) is placed in a 5-liter reactor equipped with mechanical stirrer and reflux condenser. The still-hot product in the 3-liter reactor is slowly added to the methylene chloride. This mixture is then washed with diluted hydrochloric acid. After distilling the methylene chloride, volatile components are removed using a wiped film evaporator at 200° C. and 1.0 torr vacuum. The product, Compound A, weighs 1,410 grams which is aproximately 74% of its theoretical yield.

EXAMPLE 4

Step I:
2,4,6-Tribromophenol (1,160 grams, 3.5 moles), lithium hydroxide monohydrate (7.5 grams), and ethylene glycol (2000 grams) are combined in a 5-liter reactor equipped with mechanical stirrer and subsurface gas inlet tube. The mixture is heated to 120° C. and ethylene oxide is introduced subsurface at a rate of three to four grams per minute with vigorous stirring. The pH of the reaction mixture is monitored with dampened pH indicator paper. After approximately one hour, depending on the rate of ethylene oxide addition, the pH will change from slightly acidic to strongly basic. At this point, the ethylene oxide addition is discontinued. Between 180 grams and 200 grams of ethylene oxide will have been used. When the reaction has cooled below 100° C., water (750 grams) is added. With the temperature at or still slightly above 70° C., the heavy slurry is filtered on a laboratory filtering centrifuge and washed on the filter cloth with 70° C. water (10 liter). The product is dried in a forced draft oven at 80° C. to constant weight. The product, β-hydroxyethyl-2,4,6-tribromophenyl ether, weighs 1190 grams, which is approximately 91% of the theoretical yield.

Step II:
Product from Step I (940 grams, 2.5 moles), and pyridine (3 liters) are combined in a 5-liter reactor equipped with mechanical stirrer. After cooling the mixture to <5° C., benzenesulfonyl chloride (883 grams, 5 moles) is added dropwise over one hour while keeping the temperature at <5° C. The mixture is allowed to slowly warm to room temperature after stirring for 16 hours at <5° C. After filtering off the solids formed, the mixture is slowly added to a 12-liter reactor half-full with an ice/water slurry with vigorous agitation. The product is recovered by filtration and dried in a vacuum oven to constant weight. The product, 2-(2,4,6-tribormophenoxy)-ethyl benzenesulfonate weighs 1,210 grams which is about 94% of the theoretical yield.

Step III:
Same as Step II of Example 1 except β-(2,4,6-tribromophenoxy)-ethyl benzenesulfonate (1,160 grams, 2.25 moles) is used in place of Compound Q. The product, Compound A, weighs 1540 grams which is 93% of theory. Combined yield of the three steps is approximately 79% of its theoretical yield.

We claim:
1. A halogenated unsymmetrical higher alkyl bisphenoxy alkane of the structure:

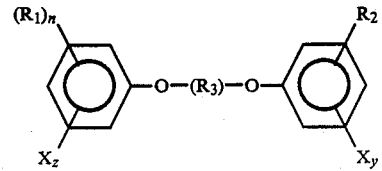

Wherein X is bromine or chlorine; $R_1$ is straight ($C_1$ to $C_{12}$) or branched alkyl selected from the group consisting of methyl ($CH_3$), ethyl ($C_2H_5$), propyl ($C_3H_7$), butyl ($C_4H_9$), pentyl ($C_5H_{11}$), hexyl ($C_6H_{13}$), heptyl ($C_7H_{15}$), octyl ($C_8H_{17}$), nonyl ($C_9H_{19}$), decyl ($C_{10}H_{21}$), undecyl ($C_9H_{19}$), and dodecyl ($C_{12}H_{25}$); z is an integer from 2 to 5; n is 0, 1, or 2; $R_2$ is a straight or branched alkyl selected from the group consisting of secondary butyl (sec $C_4H_9$), pentyl ($C_5H_{11}$), hexyl ($C_6H_{13}$), heptyl ($C_7H_{15}$), octyl ($C_8H_{17}$), nonyl ($C_9H_{19}$), decyl ($C_{10}H_{21}$), undecyl ($C_{11}H_{23}$) and dodecyl ($C_{12}H_{25}$); y is 0, 1, or 2; $R_3$ is a straight or branched alkylene group selected from the group consisting of methylene ($CH_2$), ethylene ($C_2H_4$), propylene ($C_3H_6$), butylene ($C_4H_8$), pentylene ($C_5H_{10}$), hexylene ($C_6H_{12}$), heptylene ($C_7H_{14}$), octylene ($C_8H_{16}$), nonylene ($C_9H_{18}$), decylene ($C_{10}H_{20}$), undecylene ($C_{11}H_{22}$), and dodecylene ($C_{12}H_{24}$), and if n is 1, $R_1$ is not $R_2$.

2. A composition as claimed in claim 1 wherein X is bromine.

3. A composition as claimed in claim 2 wherein $R_2$ is octyl ($C_8H_{17}$).

4. A composition as claimed in claim 2 wherein $R_2$ is nonyl ($C_9H_{19}$).

5. A composition as claimed in claim 4 wherein $R_3$ is ethylene.

6. A halogenated unsymmetrical higher alkyl bisphenoxy alkane of the structure:

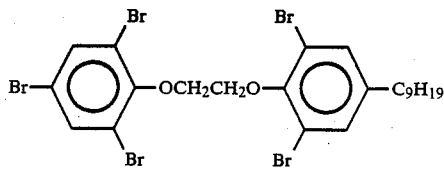

7. A halogenated unsymmetrical higher alkyl bisphenoxy alkane of the structure:

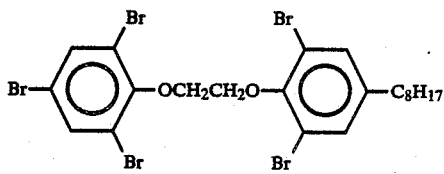

8. A halogenated unsymmetrical higher alkyl bisphenoxy alkane of the structure:

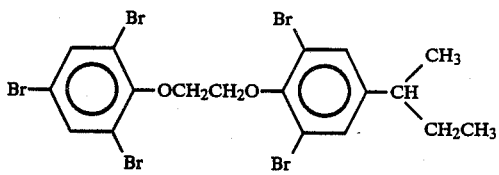

* * * * *